US006963199B2

(12) United States Patent
Sato

(10) Patent No.: US 6,963,199 B2
(45) Date of Patent: Nov. 8, 2005

(54) RARE GAS POLARIZER APPARATUS AND MAGNETIC RESONANCE IMAGING SYSTEM

(75) Inventor: Hiroshi Sato, Tokyo (JP)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 0 days.

(21) Appl. No.: 10/881,401

(22) Filed: Jun. 30, 2004

(65) Prior Publication Data

US 2005/0001615 A1  Jan. 6, 2005

(30) Foreign Application Priority Data

Jul. 3, 2003  (JP) .............................. 2003-190977

(51) Int. Cl.[7] .............................................. G01V 3/00
(52) U.S. Cl. ..................................... 324/306; 600/419
(58) Field of Search ............................... 324/306, 307, 324/309, 300; 600/411, 419, 427

(56) References Cited

U.S. PATENT DOCUMENTS

| | | | |
|---|---|---|---|
| 3,976,050 A | 8/1976 | Glasser et al. | |
| 4,093,429 A | 6/1978 | Siegler et al. | |
| 4,202,345 A | 5/1980 | Farella et al. | |
| 4,681,602 A | 7/1987 | Glenn et al. | |
| 4,751,462 A * | 6/1988 | Glover et al. | 324/309 |
| 4,844,715 A | 7/1989 | Henrich et al. | |
| 5,936,404 A * | 8/1999 | Ladebeck et al. | 324/300 |
| 5,980,608 A | 11/1999 | Dietz et al. | |
| 6,185,446 B1 * | 2/2001 | Carlsen, Jr. | 600/411 |
| 6,471,747 B1 | 10/2002 | Venkatesh et al. | |
| 6,597,939 B1 * | 7/2003 | Lampotang et al. | 600/427 |
| 6,648,130 B1 | 11/2003 | Hasson et al. | |

FOREIGN PATENT DOCUMENTS

JP  2000-507688  6/2000

* cited by examiner

Primary Examiner—Louis Arana
(74) Attorney, Agent, or Firm—Carl B. Horton, Esq.; Armstrong Teasdale LLP

(57) ABSTRACT

A rare gas polarizer apparatus includes a polarizing section for bringing a rare gas contained in a mixed gas to a hyperpolarized state, an extracting section for sublimating the rare gas from the mixed gas, extracting the rare gas as a solid, and vaporizing the extracted solid rare gas, and a supplying section for mixing the vaporized rare gas with an inspired material, and supplying the gas to a mask section that is closed against the outer air and covering the respiratory organs of the subject.

7 Claims, 6 Drawing Sheets ized state and an inspired material to a subject with quantifiability and without fail to conduct imaging.

RARE GAS POLARIZER APPARATUS AND MAGNETIC RESONANCE IMAGING SYSTEM

CROSS REFERENCE TO RELATED APPLICATIONS

This application claims the benefit of Japanese Application No. 2003-190977 filed Jul. 3, 2003.

BACKGROUND OF THE INVENTION

The present invention relates to a rare gas polarizer apparatus and a magnetic resonance imaging system for producing a rare gas in a hyperpolarized state, and conducting imaging using the rare gas.

In recent years, a magnetic resonance image is acquired with high sensitivity with a rare gas isotope such as xenon (Xe), helium (He) etc. in a hyperpolarized state absorbed in a subject by inhalation or injection. To bring the rare gas to a hyperpolarized state, a rare gas polarizer apparatus is employed.

The rare gas polarizer apparatus brings a rare gas isotope to a hyperpolarized state in a high temperature cell, and then solidifies only the rare gas in a hyperpolarized state by sublimation of the rare gas in a thermostatic bath containing liquid nitrogen under a high magnetic field environment to extract only the rare gas. The solidified rare gas is then vaporized by warming, and inhaled by the subject (for example, see Patent Document 1).

At that time, the vaporized rare gas in a hyperpolarized state is accumulated in a gas bag, vial or the like, and then inhaled by the subject from the outlet of the bag or vial.

Patent Document 1

Japanese Patent Publication No. 2000-507688 (Pages 7–19, FIG. 1).

In the conventional technique, however, the amounts of the rare gas and an inspired material such as oxygen inhaled by the subject are indefinite. Specifically, the subject's inhalation of the rare gas from the outlet of the gas bag or vial is done in various ways different from subject to subject, and also some of the rare gas may leak to the outer air without being inhaled by the subject; therefore, the amounts of the rare gas and the inspired material such as oxygen inhaled are different from examination to examination.

Especially, when the subject inhales, if only the gas contained in the gas bag or vial is inhaled, the inspired material such as oxygen becomes deficient, leading to the possibility of loss of consciousness of the subject. Moreover, the fact that the amount of the inhaled rare gas in a hyperpolarized state is indefinite may hamper quantification of magnetic resonance information such as acquired tomographic image information.

It is therefore important to find a way to implement a rare gas polarizer apparatus and a magnetic resonance imaging system that supply a rare gas in a hyperpolarized state and an inspired material to the subject with quantifiability and without fail to conduct imaging.

SUMMARY OF THE INVENTION

Therefore, an object of the present invention is to provide a rare gas polarizer apparatus and a magnetic resonance imaging system that supply a rare gas in a hyperpolarized To solve the aforementioned problem and attain the object, a rare gas polarizer apparatus in accordance with the invention of a first aspect is characterized in comprising: a polarizing section for bringing a rare gas contained in a mixed gas to a hyperpolarized state; an extracting section for sublimating said rare gas from said mixed gas, extracting said rare gas as a solid, and vaporizing said extracted solid rare gas; and supplying means for mixing said vaporized rare gas with an inspired material, and supplying said gas to a mask section closed against the outer air covering the respiratory organs of the subject.

According to the invention of the first aspect, the polarizing section brings a rare gas contained in a mixed gas to a hyperpolarized state, the extracting section sublimates the rare gas from the mixed gas, extracts the rare gas as a solid, and vaporizes the extracted solid rare gas, and the supplying means mixes the vaporized rare gas with an inspired material, and supplies the gas to a mask section closed against the outer air covering the respiratory organs of the subject; and therefore, the rare gas in a hyperpolarized state is prevented from leaking to the outer air, and the rare gas, along with the inspired material including oxygen etc., is inhaled by the subject without fail, so that a rare gas in a hyperpolarized state can be supplied to the subject with quantifiability and safety.

A rare gas polarizer apparatus in accordance with the invention of a second aspect is characterized in that: said inspired material is oxygen or air containing oxygen.

According to the invention of the second aspect, even though the closed mask section is employed, the subject can continue respiration.

A rare gas polarizer apparatus in accordance with the invention of a third aspect is characterized in that: said mask section comprises a diaphragm that is displaced synchronously with respiration of said subject.

According to the invention of the third aspect, a pressure change inside the mask section can be detected.

A rare gas polarizer apparatus in accordance with the invention of a fourth aspect is characterized in that: said mask section comprises an on-off type intake valve for taking in said vaporized rare gas and said inspired material.

According to the invention of the fourth aspect, since the mask section takes in the vaporized rare gas and inspired material through an on-off type intake valve, the intake of the vaporized rare gas and inspired material can be controlled.

A rare gas polarizer apparatus in accordance with the invention of a fifth aspect is characterized in that: said intake valve comprises regulating means for regulating the amount of intake of said rare gas and said inspired material.

According to the invention of the fifth aspect, since the intake valve regulates the amount of intake of the rare gas and inspired material by the regulating means, finer regulation on the mix ratio between the rare gas and inspired material, for example, can be achieved.

A rare gas polarizer apparatus in accordance with the invention of a sixth aspect is characterized in that: said intake valve comprises a stopper at an intake vent for said inspired material for preventing said intake vent from completely closing.

According to the invention of the sixth aspect, since the intake valve prevents the intake vent for the inspired material from completely closing by a stopper at the intake vent, the inspired material supplied to the subject is protected against stopping in some abnormal condition.

A rare gas polarizer apparatus in accordance with the invention of a seventh aspect is characterized in that: said mask section comprises an on-off type exhaust valve for discharging an expired material from said subject to said outer air.

According to the invention of the seventh aspect, since the mask section exhausts an expired material from the subject to the outer air through an on-off type exhaust valve, the expired material such as carbon dioxide can be discharged without fail.

A rare gas polarizer apparatus in accordance with the invention of an eighth aspect is characterized in that: said supplying means opens said intake valve in response to displacement of said diaphragm in synchronism with inspiration of said subject, and closes said intake valve in response to displacement of said diaphragm in synchronism with expiration of said subject. According to the invention of the eighth aspect, the rare gas and inspired material can be taken in with inspiration and the intake can be stopped by expiration, synchronously with the displacement of the diaphragm.

A rare gas polarizer apparatus in accordance with the invention of a ninth aspect is characterized in that: said supplying means closes said exhaust valve synchronously with inspiration of said subject, and opens said exhaust valve synchronously with expiration of said subject.

According to the invention of the ninth aspect, when the intake valve is open the exhaust valve is closed, and when the intake valve is closed the exhaust valve is opened, so that intake of the rare gas and discharge can be achieved efficiently and without waste.

A rare gas polarizer apparatus in accordance with the invention of a tenth aspect is characterized in that: said diaphragm comprises a detection sensor for detecting said displacement.

According to the invention of the tenth aspect, since the diaphragm detects the displacement by a detection sensor, respiration information can be obtained as an electric signal.

A rare gas polarizer apparatus in accordance with the invention of an eleventh aspect is characterized in that: said supplying means comprises a flowmeter for measuring the flow rate of said vaporized rare gas.

According to the invention of the eleventh aspect, since the supplying means measures the flow rate of the vaporized rare gas by a flowmeter, more detailed information on the amount of the inhaled rare gas can be obtained.

A magnetic resonance imaging system in accordance with the invention of a twelfth aspect comprises: a rare gas polarizer apparatus for supplying a rare gas in a hyperpolarized state to a subject, and a magnetic resonance imaging apparatus for acquiring magnetic resonance information on said subject inhaling said rare gas, and said magnetic resonance imaging system is characterized in that: said rare gas polarizer apparatus has supplying means for supplying said rare gas mixed with an inspired material to a mask section closed against the outer air covering the respiratory organs of said subject; said supplying means has a detection sensor for detecting said respiration; and said magnetic resonance imaging apparatus has a control processing section for conducting said acquisition or optimization of parameters for said acquisition based on respiration information from said detection sensor.

According to the invention of the twelfth aspect, in the rare gas polarizer apparatus, the supplying means supplies a rare gas mixed with an inspired material to a mask section closed against the outer air covering the respiratory organs of the subject; in the supplying means, the detection sensor detects the respiration; and in the magnetic resonance imaging apparatus, the control processing section conducts the acquisition or optimization of parameters for the acquisition based on respiration information from the detection sensor; therefore, quantifiability of the rare gas in a hyperpolarized state inhaled by the subject and respiration information including the inhalation allows for quantitative analysis of magnetic resonance information such as tomographic image information on the subject, and moreover, optimization of parameters including the gain or band width in acquiring the magnetic resonance information can be achieved.

A magnetic resonance imaging system in accordance with the invention of a thirteenth aspect is characterized in that: said control processing section conducts said acquisition synchronously with the inspiration or expiration indicated in said respiration information.

According to the invention of the thirteenth aspect, when tomographic image information on the subject is acquired, artifacts can be reduced; more generally, when magnetic resonance information is acquired, stable information can be obtained.

A magnetic resonance imaging system in accordance with the invention of a fourteenth aspect is characterized in that: said control processing section conducts said acquisition after an additional lag time from said synchronization.

According to the invention of the fourteenth aspect, by changing the lag time, data can be acquired in any phase of respiration.

A magnetic resonance imaging system in accordance with the invention of a fifteenth aspect is characterized in that: said control processing section counts the number of times of respiration from said respiration information and conducts said optimization on parameters based on said number of times of respiration.

According to the invention of the fifteenth aspect, information on the speed of motion of the subject based on the number of times of respiration of the subject allows parameters such as the band width and number of data acquisitions to be set for artifact reduction or high SNR.

A magnetic resonance imaging system in accordance with the invention of a sixteenth aspect is characterized in that: said parameters include the gain of an amplifier for use in acquiring said magnetic resonance information.

According to the invention of the sixteenth aspect, a gain when the rare gas in a hyperpolarized state is inhaled can be optimized from a gain in a prescan.

A magnetic resonance imaging system in accordance with the invention of a seventeenth aspect is characterized in that: said supplying means further comprises a flowmeter for measuring the flow rate of said rare gas.

According to the invention of the seventeenth aspect, since the supplying means measures the flow rate of the rare gas by a flowmeter, more detailed information on the amount of the inhaled rare gas can be obtained.

A magnetic resonance imaging system in accordance with the invention of a seventeenth aspect is characterized in that: said control processing section conducts said optimization of parameters based on flow rate information from said flowmeter.

According to the invention of the eighteenth aspect, since detailed information on the amount of the rare gas inhaled by the subject is obtained, adjustment of the gain of the amplifier and other-such tuning can be more finely conducted based on the detailed information.

According to the present invention, the polarizing section brings a rare gas contained in a mixed gas to a hyperpolarized state, the extracting section sublimates the rare gas from the mixed gas, extracts the rare gas as a solid, and vaporizes the extracted solid rare gas, and the supplying means mixes the vaporized rare gas with an inspired material, and supplies the gas to a mask section closed against the outer air covering the respiratory organs of the subject; and therefore, the rare gas in a hyperpolarized state is prevented from leaking to the outer air, and the rare gas, along with the inspired material including oxygen etc., is inhaled by the subject without fail, so that a rare gas in a hyperpolarized state can be supplied to the subject with quantifiability and safety.

Further objects and advantages of the present invention will be apparent from the following description of the preferred embodiments of the invention as illustrated in the accompanying drawings.

DETAILED DESCRIPTION OF THE INVENTION

Preferred embodiments of a rare gas polarizer apparatus and a magnetic resonance imaging system in accordance with the present invention will now be described with reference to the accompanying drawings.

(Embodiment 1)

Figure 1:
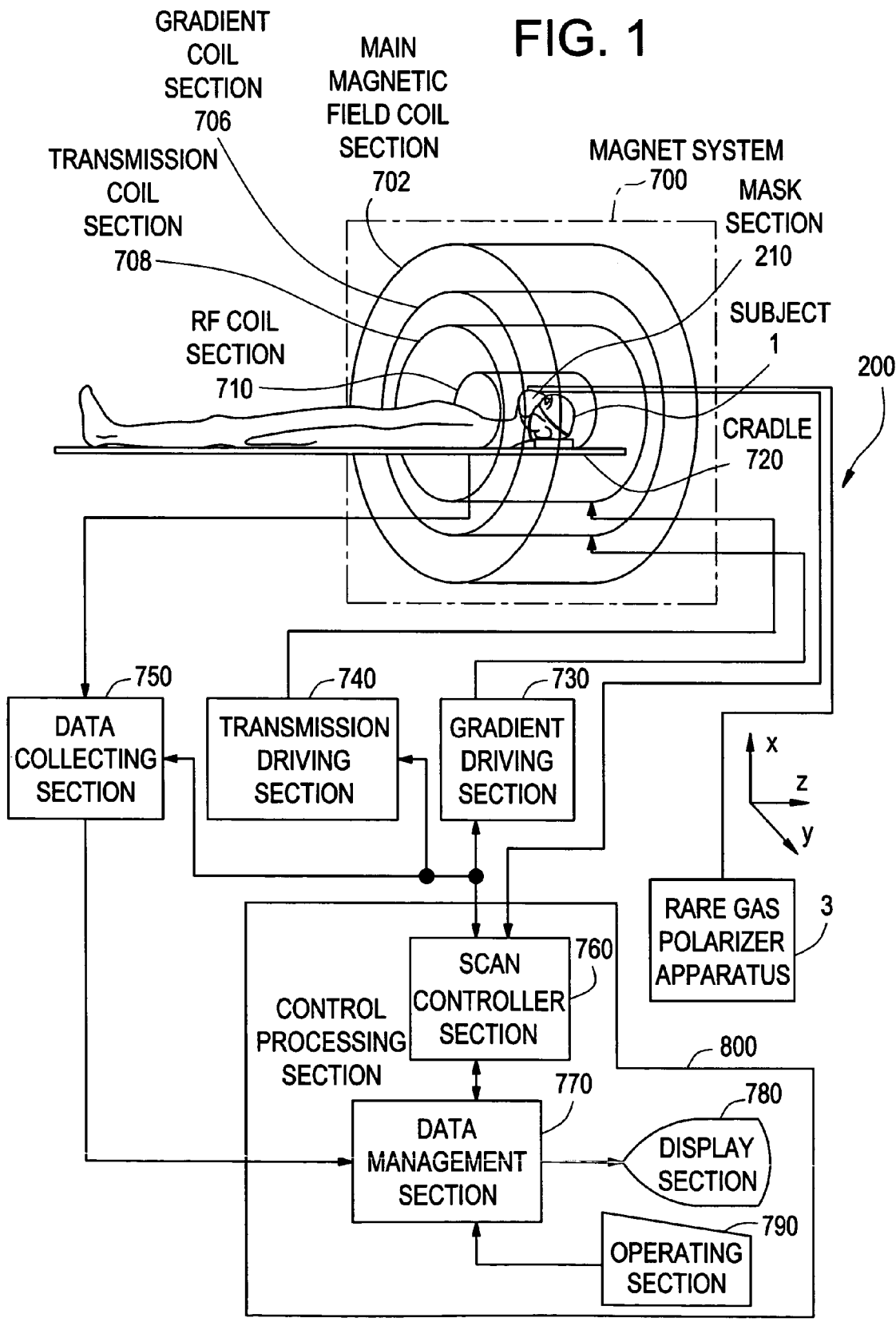
FIG. 1 is a block diagram showing the overall configuration of a magnetic resonance imaging system.

First, the overall configuration of a magnetic resonance imaging system in accordance with Embodiment 1 will be described. FIG. 1 is a block diagram showing the overall configuration of the magnetic resonance imaging system of the present invention. The magnetic resonance imaging system comprises a magnetic resonance imaging apparatus 200 and a rare gas polarizer apparatus 3.

The magnetic resonance imaging apparatus 200 comprises a magnet system 700, a data collecting section 750, a transmission driving section 740, a gradient driving section 730 and a control processing section 800. The control processing section 800 comprises a scan controller section 760, a data management section 770, a display section 780 and an operating section 790.

The magnet system 700 has a main magnetic field coil section 702, a gradient coil section 706, a transmission coil section 708 and an RF coil section 710. These coil sections have a generally cylindrical shape and are concentrically disposed with respect to one another. A subject 1 rested on a cradle 720 is carried into and out of a generally cylindrical internal space (bore) of the magnet system by carrier means (not shown).

In such a configuration, control information is input from the operating section 790 to the data management section 770, and the control information is transferred to the scan controller section 760, then from the scan controller section 760 to the data collecting section 750, and output to the transmission driving section 740 and gradient driving section 730.

The main magnetic field coil section 702 generates a static magnetic field in the internal space of the magnet system 700. The direction of the static magnetic field is generally parallel to the direction of the body axis of the subject 1. That is, a magnetic field generally called a horizontal magnetic field is generated. The main magnetic field coil section 702 is made using a superconductive coil, for example; however, it is not limited to the superconductive coil but may be made using a normal conductive coil or the like.

The gradient coil section 706 generates three gradient magnetic fields for imparting gradients to the static magnetic field intensity along three mutually orthogonal axes, i.e., a slice axis, a phase axis and a frequency axis.

The transmission coil section 708 generates a radio frequency magnetic field for exciting magnetic resonance within the subject 1 in the static magnetic field space. The RF coil section 710 is placed on the cradle 720, and is positioned in the central portion of the magnet system 700 along with the subject 1. The RF coil section 710 receives magnetic resonance signals excited by the transmission coil section 708 within the subject 1.

The gradient coil section 706 is connected to the gradient driving section 730. The gradient driving section 730 transmits a driving signal to the gradient coil section 706 to generate the gradient magnetic fields. The gradient driving section 730 has three driving circuits (not shown) corresponding to the three gradient coils in the gradient coil section 706.

The transmission coil section 708 is connected to the transmission driving section 740. The transmission driving section 740 supplies a driving signal to the transmission coil section 708 to transmit an RF pulse, and the transmission coil section 708 then generates the RF magnetic field in the central portion of the magnet system 700 in response to the transmitted RF pulse to bring the subject 1 to a magnetic resonance excited state.

The RF coil section 710 is connected to the data collecting section 750. The data collecting section 750 takes in a received signal received at the RF coil section 710 by sampling it, and collects the signal as digital data.

The gradient driving section 730, transmission driving section 740 and data collecting section 750 are connected to the scan controller section 760. The scan controller section 760 serving as a reception control section controls the gradient driving section 730, transmission driving section 740 and data collecting section 750 to conduct imaging.

The output of the data collecting section 750 is connected to the data management section 770. Data collected by the data collecting section 750 is input to the data management section 770. The data management section 770 is made using, for example, a computer, and has a memory (not shown). The memory stores programs and several kinds of data for the data management section 770.

The data management section 770 is connected to the scan controller section 760. The data management section 770 is upstream of the scan controller section 760 and controls it. Acquisition of magnetic resonance information including tomographic image information in the present apparatus is implemented by executing at the scan controller section 760 a pulse sequence that is a program stored in the memory in the data management section 770. The pulse sequence contains a sequence of all of control information output to the gradient driving section 730, transmission driving section 740 and data collecting section 750.

The data management section 770 stores the data collected by the data collecting section 750 into the memory. In the memory, a data space is thus formed. The data space forms a two-dimensional Fourier space. The data management section 770 performs two-dimensional inverse Fourier transformation on the data in the two-dimensional Fourier space to reconstruct an image of the subject 1.

The data management section 770 is connected to the display section 780 and operating section 790. The display section 780 comprises a graphic display such as an LCD (liquid crystal display). The operating section 790 comprises a keyboard provided with a pointing device, for example.

The display section 780 displays the reconstructed image and several kinds of information output from the data management section 770. The operating section 790 is operated by a human operator, and inputs several kinds of instructions and information to the data management section 770. The operator interactively operates the present apparatus via the display section 780 and operating section 790.

The RF coil section 710 comprises a birdcage coil, for example, for receiving a magnetic resonance signal excited within the subject 1.

The rare gas polarizer apparatus 3 supplies a hyperpolarized rare gas, for example, isotope xenon (Xe), to the subject 1. The hyperpolarized state will now be briefly described. Isotope rubidium (Rb) or xenon that is a rare gas has a nuclear magnetic moment, and when a static magnetic field is applied, the gas is distributed among different energy states. In a normal temperature equilibrium state, isotope rubidium or xenon is distributed generally equally among all the states. On the contrary, a state in which much of isotope rubidium or xenon is disproportionally present in a certain state is called a hyperpolarized state. In the hyperpolarized state, more of isotope rubidium or xenon can be brought to an excited state of a magnetic resonance phenomenon, thereby improving signal sensitivity.

The rare gas polarizer apparatus 3 supplies gaseous xenon in a hyperpolarized state to the subject 1 via a mask section 210 attached to the subject 1. The subject 1 inhales the xenon, and takes it into the blood via the lungs. Then, magnetic resonance imaging can be conducted on the subject 1 to image xenon with high sensitivity.

Figure 2:
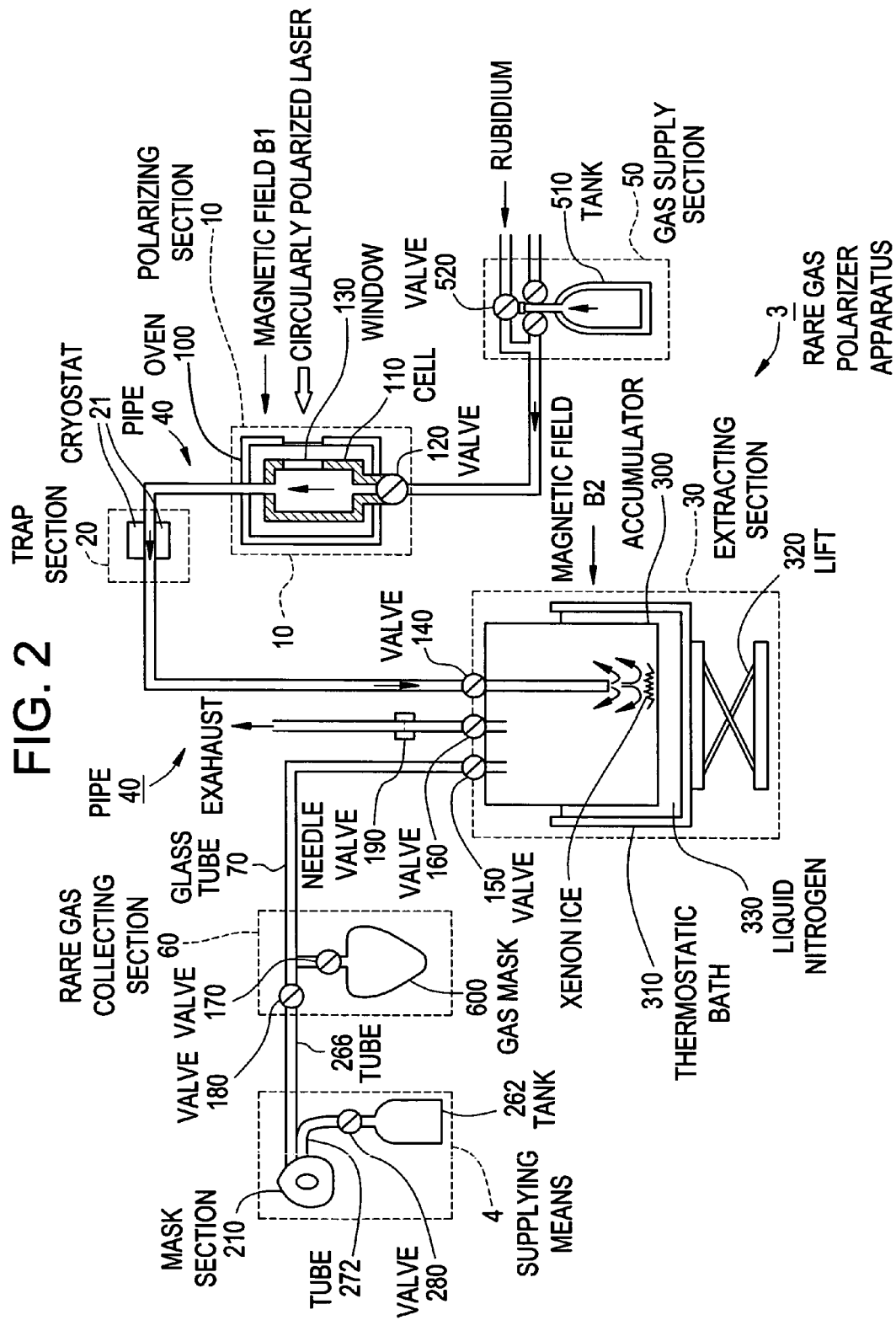
FIG. 2 is a block diagram showing the configuration of a rare gas polarizer apparatus in Embodiment 1.

Next, the configuration of the rare gas polarizer apparatus 3 will be described in detail with reference to FIG. 2. FIG. 2 is a diagram showing a configuration of several blocks in the rare gas polarizer apparatus 3 and cross sections of the blocks. The rare gas polarizer apparatus 3 comprises a gas supply section 50, a polarizing section 10, a trap section 20, an extracting section 30, a rare gas collecting section 60, supplying means 4, a pipe 40 for connecting the polarizing section 10, trap section 20 and extracting section 30, a glass tube 70 for connecting the extracting section 30 and rare gas collecting section 60, and a tube 266 for connecting the rare gas collecting section 60 and supplying means 4. In such a configuration, a static magnetic field B1 and a static magnetic field B2 are applied to the polarizing section 10 and extracting section 30, which static magnetic fields are generated by a permanent magnet (not shown), for example.

The gas supply section 50 is comprised of an on-off valve 520 for regulating supply of isotope rubidium from the outside, a tank 510, and a metal pipe for supplying a mixed gas to the polarizing section 10. The tank 510 stores a mixed gas of xenon isotope, nitrogen and helium (He), approximately in a proportion of 1%, 1%, 98%, compressed under a high pressure. The mixed gas is mixed with isotope rubidium at the outlet of the tank 510, and then led to the polarizing section 10.

The polarizing section 10 comprises a cell 110, an oven 100 and a valve 120. The oven 100 contains therein the cell 110, and places the cell 110 under a high temperature of about 200° C. The polarizing section 10 is irradiated with a circularly polarized laser light. The laser light is generated by a laser diode array (not shown), for example, and has a wavelength determined by an alkali metal contained in the mixed gas. For example, for rubidium, the wavelength is about 795 nm (nanometers). The oven 100 and cell 110 have respective glass windows for letting the laser light into the cell 110.

The valve 120 is an on-off valve, and the mixed gas produced at the gas supply section 50 is led into the cell 110 by opening the valve 120. The cell 110 is comprised of an internal cavity for making the mixed gas interact with the circularly polarized laser, and an interior wall and an exterior wall surrounding the internal cavity. The interior wall is made of glass, and the exterior wall is made of a stainless steel, for example.

The exterior wall of the cell 110 on the side surface exposed to the circularly polarized laser is provided with a window 130 of refractory glass. The circularly polarized laser light passing through the window of the oven 100 and the window 130 enters the cell 110, and interacts with the mixed gas. The pipe 40 carries the mixed gas in the cell 110 to the extracting section 30 through the trap section 20.

The trap section 20 has a cryostat 21 on an interior wall of glass of the pipe 40. The cryostat 21 is a cooling pipe carrying water wound around the interior wall of the pipe 40, for example. The mixed gas within the interior wall is thus cooled, and gaseous rubidium in the mixed gas is liquefied and solidified for removal.

The extracting section 30 comprises an accumulator 300, a thermostatic bath 310, a liquid nitrogen 330, a lift 320, a needle valve 190 and valves 140–160. The accumulator 300 is supported by a supporting implement (not shown), and the position of the accumulator 300 relative to the thermostatic bath 310 can be arbitrarily set by the operator.

The accumulator 300 is supplied with the mixed gas from the trap section 20 through the pipe 40. The vessel of the accumulator 300 has an interior wall of glass and an exterior wall of metal, similarly to the cell 110 and pipe 40.

The accumulator 300 and the pipe 40 are separable, and only the glass tube portion of the interior wall of the pipe 40 extends as an inlet to the accumulator 300. The glass tube portion has a length such that when the accumulator 300 is attached with the pipe 40, the glass tube portion reaches the bottom of the accumulator 300, and thus the mixed gas in the pipe 40 is sprayed directly onto the bottom of the accumulator 300.

Moreover, the accumulator 300 has in its upper portion an exhaust for discarding the remaining gas, and a connection port to the rare gas collecting section 60. The exhaust is attached with the valve 160 of an on-off type and the needle valve 190 via a metal tube, for example. The needle valve 190 has a partition provided with a needle hole for separating an inlet and an outlet. The accmulator 300 can thus be kept at a high pressure at the inlet side of the needle valve 190 and at an atmospheric pressure at the outlet side after opening the valve 160.

The thermostatic bath 310 comprises a Dewar vessel, for example, and stores therein liquid nitrogen 330 for cooling the accumulator 300. Moreover, the thermostatic bath 310 is mounted on the lift 320 so that when the lift 320 is moved up, the accumulator 300 is immersed in the liquid nitrogen 330, and when the lift 320 is moved down, the accumulator 300 and liquid nitrogen 330 are separated.

The rare gas collecting section 60 is connected with the accumulator 300 via the valve 150 and glass tube 70, and the section 60 comprises a gas bag 600, and on-off valves 170 and 180. The gas bag 600 is removable from the on-off valve 170, and is used when extracted gaseous xenon in a hyperpolarized state is inhaled by the subject.

The supplying means 4 comprises the mask section 210, a tube 272, a tank 262 and a valve 280. The supplying means 4 is supplied with the rare gas from the gas bag 600 via the tube 266, and it in turn supplies the rare gas to the mask section 210. The tank 262 stores therein an inspired material containing air, oxygen gas or the like, and supplies the inspired material to the mask section 210 by opening the valve 280. It should be noted that the tube 272 is preferably made of a material other than metal so that it will not cause depolarization.

Figure 3A:
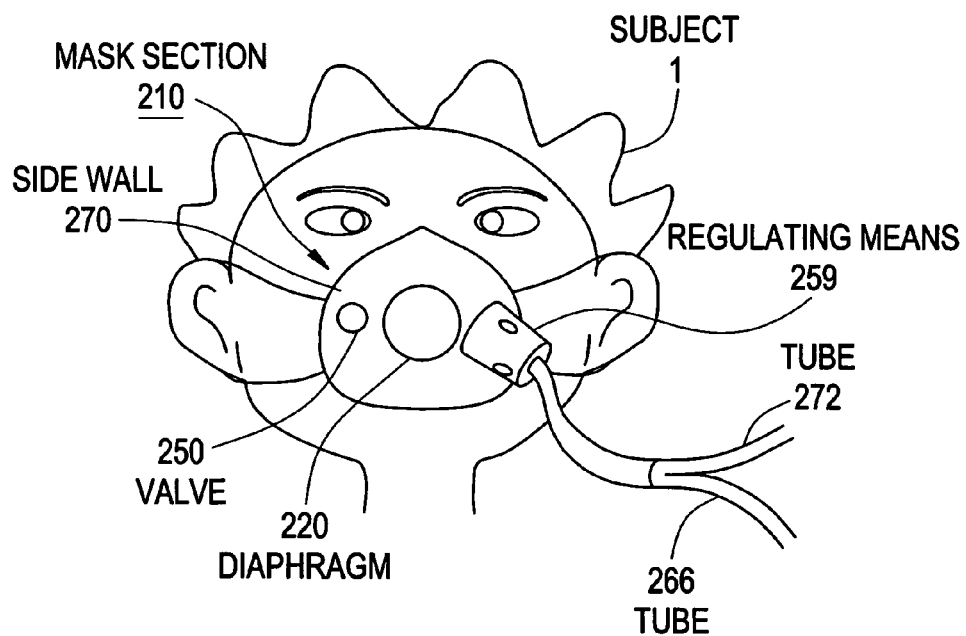
FIG. 3 is a diagram showing the configuration of a mask section in Embodiment 1.

FIG. 3 is a diagram of the mask section 210 showing its use and detailed configuration. FIG. 3(A) shows the mask section 210 attached to the subject 1. The mask section 210 is attached to the head of the subject 1 to cover the respiratory organs, i.e., the nose and mouse, of the subject 1 by a belt or the like.

Figure 3B:
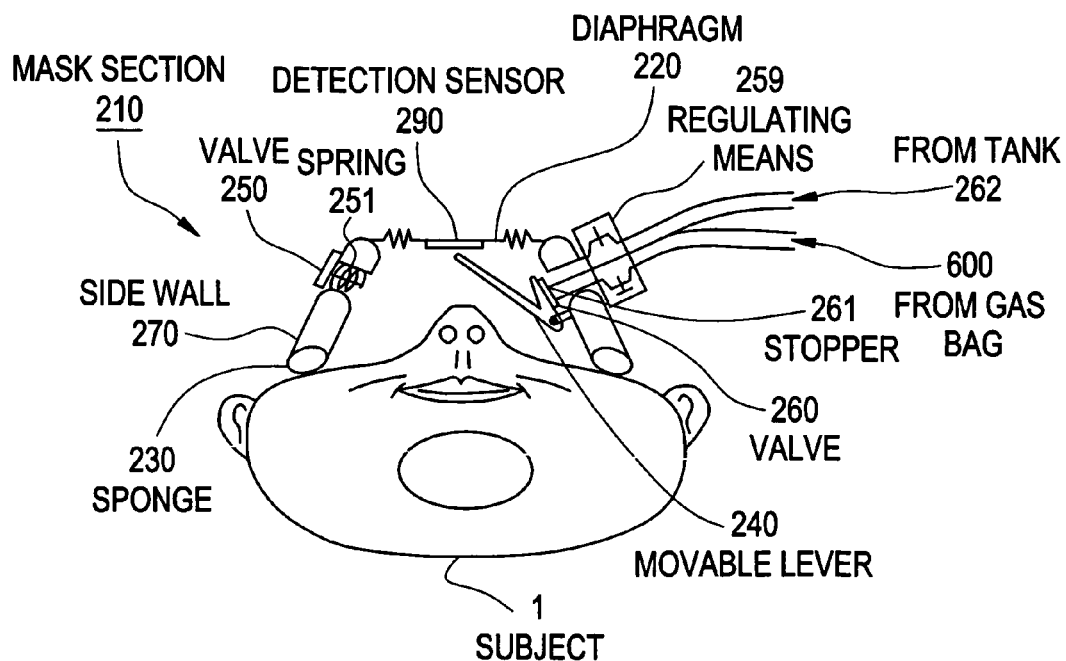

FIG. 3(B) shows the mask section 210 attached to the subject 1 in cross section. The mask section 210 comprises a side wall 270, a diaphragm 220, a sponge 230, valves 250 and 260, regulating means 259, a movable lever 240 and a detection sensor 290. The side wall 270 and diaphragm 220 have a bowl-like structure with a bottom of the diaphragm 220, and an open side opposite to the diaphragm 220 is in close contact with the face of the subject 1 including the nose and mouse.

The open side of the side wall 270 is provided with the sponge 230 to improve closeness with the face of the subject 1. The internal space surrounded by the side wall 270, diaphragm 220 and face of the subject 1 is thus closed against the outer air. The material used for the side wall 270 is a light weight and deformation-proof one such as a plastic, and the material used for the diaphragm 220 is an elastic one such as a rubber sheet. Thus, as respiration of the subject 1 causes the internal space of the mask section 210 to alternate between positive and negative pressures relative to the outer air, the diaphragm 220 deforms in response to the positive and negative pressures.

The side wall 270 is attached with the valve 250 and tube 266. The valve 250 serving as an exhaust valve is placed on the side wall 270 in a hole running from the internal space to the outer air, on the side of the outer air, and is in close contact with the side wall 270 from the side of the outer air by a spring 251. The tubes 266 and 272 are led from a hole running through the side wall 270 into the internal space via the regulating means 259. The side wall 270 is provided with a stopper 261, a valve 260 serving as an intake valve, and a movable lever 240 at the outlets of the tubes 266 and 272 to the internal space.

The regulating means 259 is a control valve for controlling the in-tube flow rate of the tubes 266 and 272, and controls the mix ratio or absolute amounts of the rare gas and inspired material by the valve set at the intermediate state between open and close.

The movable lever 240 moves the valve 260 serving as an intake valve in response to deformation of the diaphragm 220, and opens and closes the outlets of the tubes 266 and 272 to the internal space. The movable lever 240 is a V-shaped lever having a center of rotation at an intersection of two branches fixed on the side wall 270, and one of the two branches extending from the center of rotation is in contact with the surface of the diaphragm 220, and the other forms a surface to which the valve 260 is attached.

The stopper 261 is placed between the valve 260 and outlet of the tube 272 to the internal space. The stopper 261 is kept at a slightly open state so that the inspired material such as oxygen is not cut off when the valve 260 closes the outlet of the tube 272. The subject 1 is thus protected against oxygen deficit in some abnormal condition.

The diaphragm 220 is provided with the detection sensor 290. For the detection sensor 290, a distortion sensor such as a strain gauge may be used. The detection sensor 290 is connected to the scan controller section 760 via wiring (not shown), and an electric signal in synchronism with respiration of the subject 1 is transmitted to the scan controller section 760.

Now the operation of the rare gas polarizer apparatus 3 and supplying means 4 in accordance with the present invention will be described. The operation of extracting isotope xenon in a hyperpolarized state at the accumulator 300 will first be briefly described. In conducting the extracting operation, the lift 320 is moved up to immerse the accumulator 300 in the liquid nitrogen 330, water is run into the cryostat 21 in the trap section 20 to bring the trap section 20 into an operating state, a circularly polarized laser is emitted toward the cell 110, the internal space of the oven 100 containing the cell 110 is brought to a temperature of about 200° C., a static magnetic field B1 of about 10 mT (Tesla) is applied to the polarizing section 10, and a static magnetic field B2 of about 0.2 T is applied to the extracting section 30.

Then, the valves 520, 120, 140 and 160 are opened, and the valve 150 is closed. The mixed gas containing isotope rubidium produced at the gas supply section 50 is thus led into the cell 110.

In the cell 110, isotope rubidium in the mixed gas absorbs the irradiated circularly polarized laser and is brought to a hyperpolarized state in which much of the rubidium isotope is at a high energy state. Then, the rubidium isotope in a hyperpolarized state transfers the hyperpolarized state to isotope xenon in the mixed gas by a phenomenon known as spin exchange transfer. The isotope xenon is thus brought to a hyperpolarized state in which much of the isotope xenon is at a high energy state.

Thereafter, the mixed gas in the cell 110 is led to the trap section 20, where the cryostat 21 lowers the temperature of the mixed gas to remove the rubidium isotope by liquefaction or solidification.

The mixed gas at the trap section 20 is then led into the accumulator 300 via the pipe 40. The mixed gas is sprayed directly onto the bottom of the accumulator 300 via the extension tube of the pipe 40. Since the bottom of the accumulator 300 is immersed in the liquid nitrogen 330 in the thermostatic bath 310 and is at about the liquid nitrogen temperature, the isotope xenon in the mixed gas sprayed there solidifies by sublimation into xenon ice.

The other components in the mixed gas, i.e., helium gas and nitrogen gas, do not solidify, and are discarded from the accumulator 300 via the needle valve 190. Such a process continuously occurs while supplying the mixed gas from the tank 510 to accumulate xenon ice.

Next, the operation of taking out xenon in a hyperpolarized state accumulated in the accumulator 300 to the gas bag 600 will be described. In conducting the take-out operation, the valves 520, 120, 140, 160 and 180 are closed, the valves 150 and 170 are open, the lift 320 is moved down, and the liquid nitrogen 330 in the thermostatic bath 310 is not in contact with the accumulator 300.

Since the accumulator 300 is not in contact with the liquid nitrogen 330, it assumes a high temperature state. At that time, xenon ice in a hyperpolarized state present at the bottom of the accumulator 300 vaporizes by sublimation, and the vaporized isotope xenon is led from the valve 150 into the gas bag 600 via the glass tube, and accumulated there. This condition is maintained until the xenon ice present at the bottom of the accumulator 300 is spent.

The xenon in a hyperpolarized state accumulated in the gas bag 600 is then supplied to the mask section 210 attached to the subject 1. At that time, the valve 150 is closed, and the valves 170 and 180 are opened. Thus, the gaseous xenon in a hyperpolarized state in the gas bag 600 is gradually carried to the mask section 210. Moreover, the valve 280 of the tank 262 is opened, so that the inspired material such as oxygen contained in the tank 262 is simultaneously led to the mask section 210. The amounts of the xenon and inspired material such as oxygen led to the mask section 210 are regulated by the regulating means 259.

Next, the operation of the mask section 210 when the subject 1 respires will be described with reference to FIG. 4. FIG. 4 is a diagram showing the subject 1 attached with the mask section 210 in cross section. Respiration of the subject 1 is divided into an inspiring state in which the air is taken into the lungs, and an expiring state in which the air is discharged from the lungs.

Figure 4A:
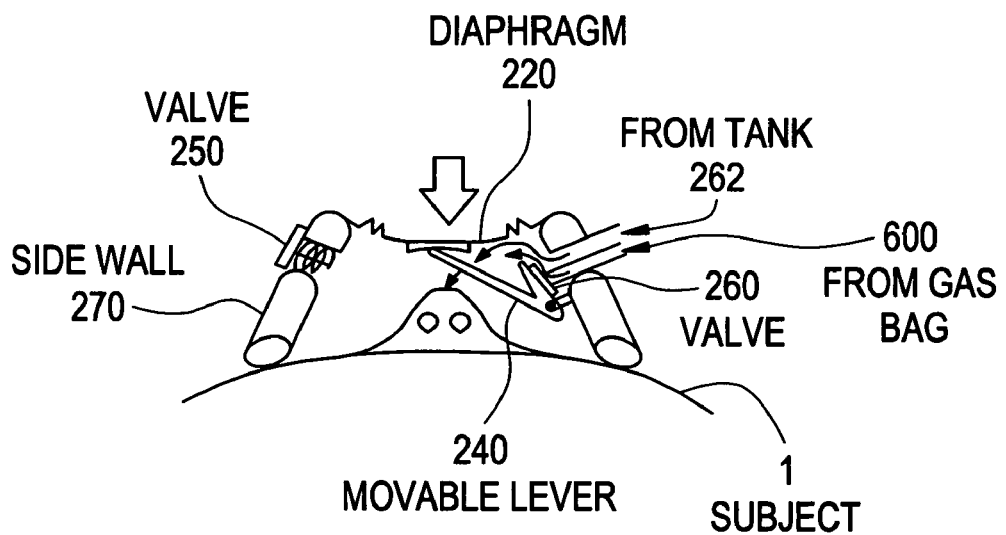
FIG. 4 is a diagram showing the operation of the mask section in Embodiment 1.

FIG. 4(A) is a diagram showing the operation of the mask section 210 when respiration of the subject 1 is in an inspiring state. The internal space of the mask section 210 is at a negative pressure relative to the outer air because of inspiration of the subject 1. Thus, the diaphragm 220 deforms to be pushed toward the subject 1. At that time, the movable lever 240 fixed at the side wall 270 rotates synchronously with the deformation of the diaphragm 220, and opens the valve 260. While the inspiring state is maintained, gaseous xenon in a hyperpolarized state and the inspired material such as oxygen are supplied from the open valve 260 at a generally constant flow rate. The valve 250 closes by being pushed from the outside against the side wall 270 with the aid of the effect of the spring 251 because the internal space is at a negative pressure relative to the outer air.

Moreover, since the internal space of the mask section 210 at that time has a small volume relative to the amount of one cycle of inspiration of the subject 1, the rare gas and inspired material containing oxygen and the like supplied from the valve 260 are largely inhaled by the subject 1. Therefore, the rare gas supplied from the tube 266 is inhaled by the subject 1 without leaking, and the amount of the rare gas inhaled by the subject 1 is largely determined by the regulating means 259.

Figure 4B:
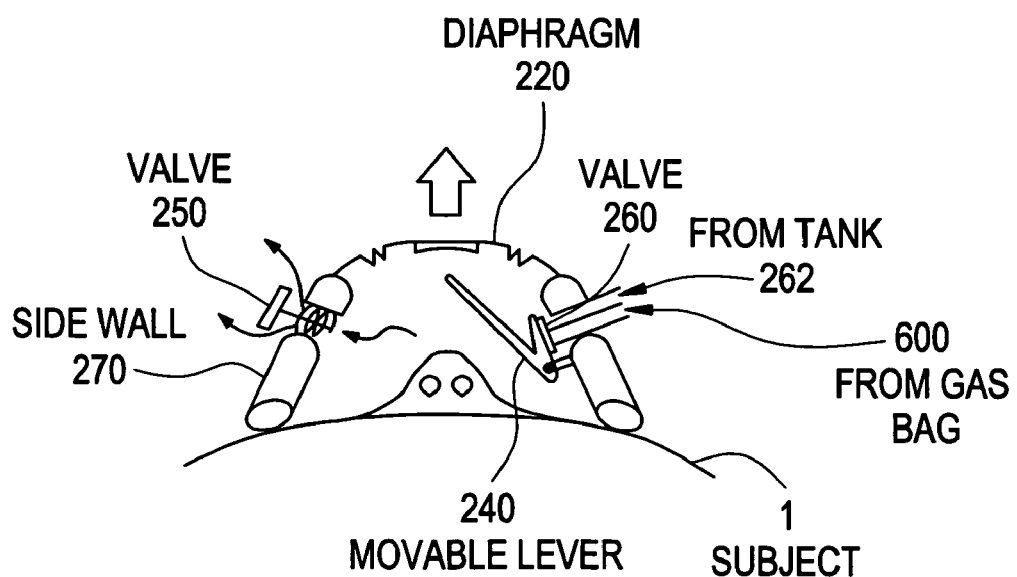

FIG. 4(B) is a diagram showing the operation of the mask section 210 when respiration of the subject 1 is in an expiring state. The internal space of the mask section 210 is at a positive pressure relative to the outer air because of expiration of the subject 1. Thus, the diaphragm 220 deforms to be pushed in a direction opposite to the subject 1. At that time, the movable lever 240 fixed at the side wall 270 moves synchronously with the deformation of the diaphragm 220 until the valve 260 is closed, and thereafter, stops and keeps the closed state. Moreover, the valve 250 is pushed toward the outside against the pressure by the spring 251 because the internal space is at a positive pressure, and discharges the expired air containing carbon dioxide and the like of the subject 1 in the internal space.

As described above, in Embodiment 1, gaseous xenon in a hyperpolarized state in the gas bag 600 and the inspired material such as oxygen are supplied to the mask section 210 in a closed state, and a positive or negative pressure in the internal space of the mask section 210 during expiration or inspiration is detected at the diaphragm 220, and discharge from the internal space or intake of xenon and the inspired material such as oxygen to the internal space is conducted based on the detection; and therefore, gaseous xenon in a hyperpolarized state is prevented from leaking to the outer air before being inhaled by the subject 1 and is supplied at a generally constant flow rate and with high quantifiability, and in addition, the inspired material such as oxygen is supplied to the subject 1 without fail, ensuring high safety.

(Embodiment 2)

While the diaphragm 220 deforms synchronously with expiration and inspiration of the subject 1 and respiration is detected by the detection sensor 290 attached on the diaphragm 220 in Embodiment 1, the detected signal can be used to quantitatively analyze acquired image information. Embodiment 2 addresses analysis of a magnetic resonance signal based on such a detected signal of respiration and information of xenon in a hyperpolarized state supplied with quantifiability.

Since the hardware configuration of the rare gas polarizer apparatus 3 around the mask section 210 and magnetic resonance imaging apparatus 200 is identical to that shown in FIGS. 1–3, detailed description thereon will be omitted here.

Figure 5A:
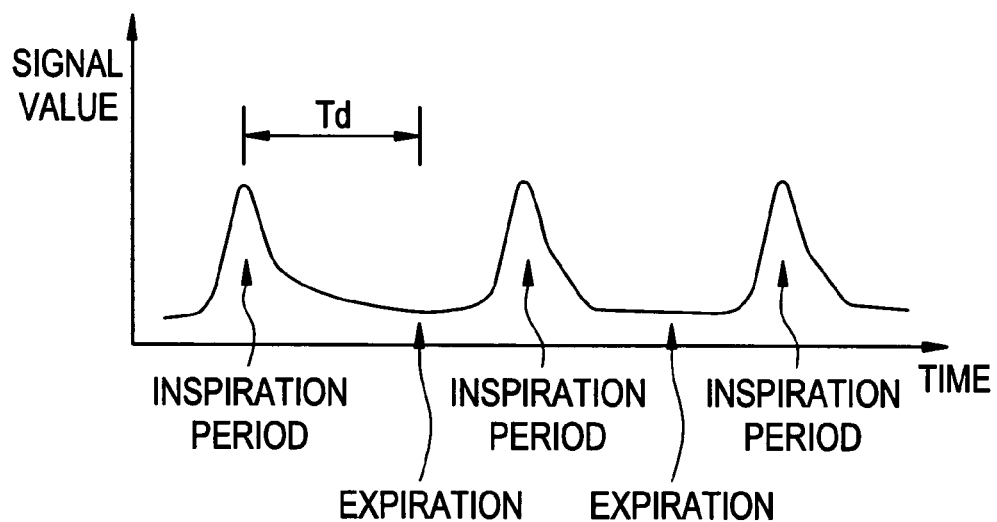
FIG. 5 is a diagram showing a respiration signal and magnetic resonance information in Embodiment 2.

FIG. 5(A) is an exemplary respiration signal, detected by the detection sensor 290, that synchronizes with respiration of the subject 1. In a respiration signal region having a high signal value, the subject 1 is in an inspiring state, and in a respiration signal region having a low signal value, the subject 1 is in an expiring state. It should be noted that the expiring state has body motion of the subject 1 slower than the inspiring state, and the expiring state continues longer than the inspiring state.

A pulse sequence read from the data management section 770 to the scan controller section 760 is sequentially decoded and executed. At that time, the pulse sequence is executed synchronously with the respiration signal from the detection sensor 290. In the case of the respiration signal exemplarily shown in FIG. 5(A), an inspiration period is detected by thresholding or peak detection, for example, and the execution of the pulse sequence and data collection are conducted after a lag time Td from the inspiration period. By defining a plurality of lag times Td, for example, a temporal change of a process of, starting from the inspiration period in which xenon in a hyperpolarized state is inhaled, absorption of xenon by the subject 1, dissolution of xenon into blood and diffusion throughout the whole body can be observed.

Figure 5B:
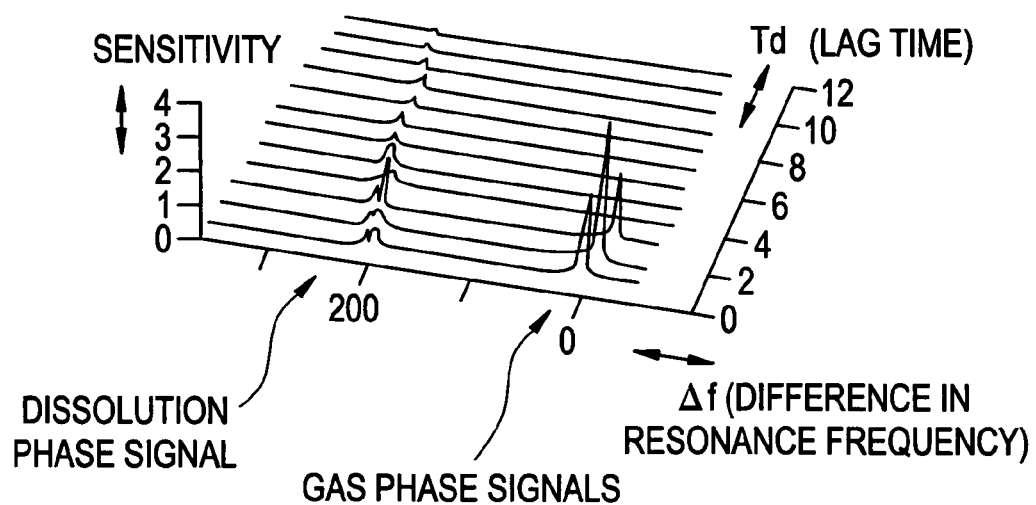

FIG. 5(B) represents in a three-dimensional manner spectrum intensity of an RF signal received from the subject 1 as a function of the lag time Td. The three axes represent the lag time Td, difference of spectrum frequency $\Delta f$, and spectrum intensity, and the plot shows, at each lag time Td, variation of the spectrum with an increasing lag time.

In the plot, a gas phase signal indicating xenon in a hyperpolarized state present in the lungs as gas and a dissolution signal indicating xenon in a hyperpolarized state present dissolved into blood have different spectrum frequencies, and are separately observed. As the lag time Td increases, xenon diffuses throughout the whole body and the intensity of the gas phase signal and dissolution signal gradually decreases. At that time, as xenon inhaled into the lungs as gas is absorbed into blood via the alveoli, a peak appears first in the gas phase signal and then in the dissolution phase signal, along the time axis of the lag time Td. Since xenon inhaled into the lungs can be quantitatively estimated, information on the gas phase signal and dissolution signal can be collected and analyzed with quantifiability.

As described above, in Embodiment 2, the detection sensor 290 detects the inspiration period, and a pulse sequence is executed after a lag time Td from the inspiration period to collect data, and therefore, data collection synchronous with the phase of respiration of the subject 1 can be conducted, and a process of xenon in a hyperpolarized state being absorbed in the subject 1 over time can be tracked dynamically and with quantifiability.

Moreover, while in Embodiment 2, the lag time Td is changed to dynamically track the change of the spectrum intensity, the lag time Td may be fixed to acquire stable tomographic image information with reduced artifacts. As can be seen from FIG. 5(A), the expiring state is longer and has less body motion than the inspiring state. Therefore, in acquiring tomographic image information using xenon in a hyperpolarized state, tomographic image information with reduced motion artifacts can be obtained by setting the lag time Td at the time position in the expiring state.

Furthermore, while in Embodiment 2, a pulse sequence is executed with reference to the respiration signal of the subject 1 as shown in FIG. 5(A), it is possible to obtain information on the number of times of respiration from the respiration signal, and optimize the pulse sequence based on the information on the number of times of respiration. In such optimization, the band width, matrix size and the like can be set depending upon the information on the number of times of respiration so that artifacts are reduced or the SNR (signal-to-noise ratio) is improved.

Moreover, while in Embodiment 2, a pulse sequence is executed synchronously with the respiration signal of the subject 1 as shown in FIG. 5(A), a respiration signal at the time of execution of the pulse sequence can be appended as additional information to collected data of a magnetic resonance signal. Thus, data selection or image processing can be applied to the collected data based on the respiration signal after the data collection.

(Embodiment 3)

While xenon in a hyperpolarized state and the inspired material such as oxygen are supplied to the closed mask section 210 to achieve supply of xenon with quantifiability in Embodiment 1, the tube 266 for conveying gaseous xenon may be provided with a flowmeter to further improve quantifiability, and optimize parameters such as a gain in data collection using xenon in a hyperpolarized state.

Figure 6:
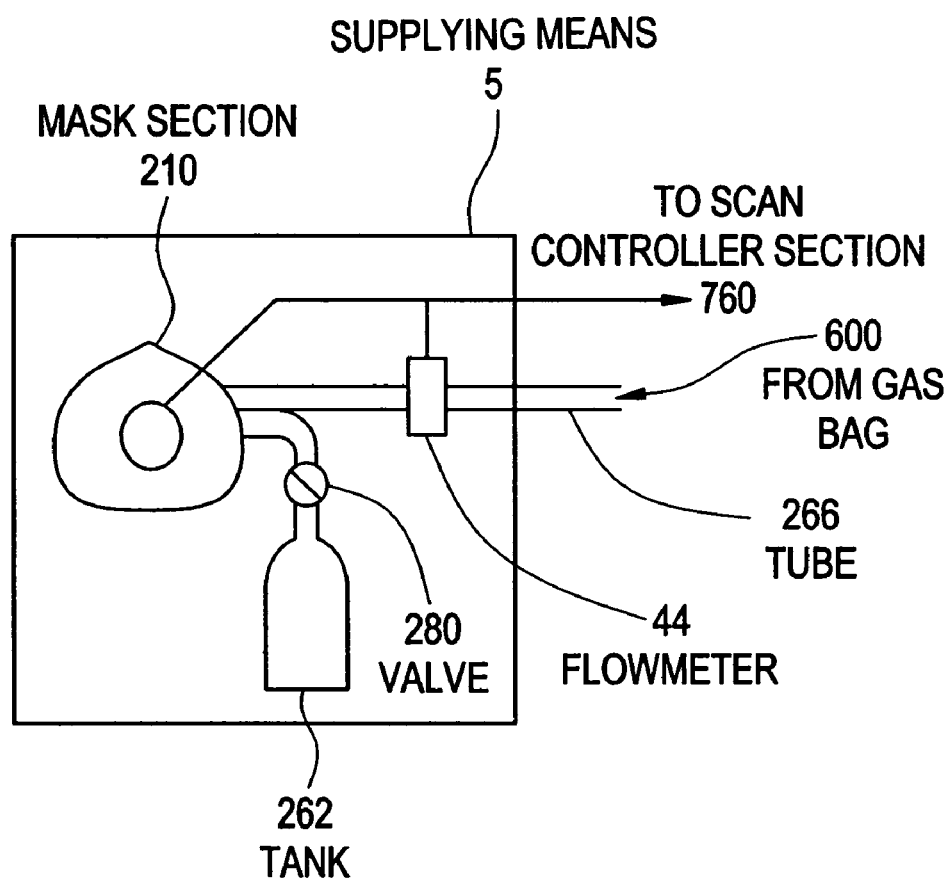
FIG. 6 is a diagram showing the configuration of supplying means in Embodiment 3.

FIG. 6 is a diagram showing supplying means 5 in accordance with Embodiment 3. The magnetic resonance imaging apparatus 200, and the gas supply section 50, polarizing section 10, trap section 20, extracting section 30 and rare gas collecting section 60 in the rare gas polarizer apparatus 3 are identical to those shown in FIGS. 1 and 2, and detailed description thereon will be omitted.

The supplying means 5 in FIG. 6 comprises the mask section 210, tube 272, tank 262, valve 280, and a flowmeter 44. The mask section 210, tube 272, tank 262 and valve 280 are identical to those of the supplying means 4, and detailed description thereon will be omitted. The flowmeter 44 is attached to the tube 266, and it measures the flow rate of the rare gas flowing in from the gas bag 600. The measured flow rate is transmitted to the scan controller section 760 along with the respiration signal from the mask section 210.

The flowmeter 44 may be one that simply obtains the flow rate by using, for example, an orifice plate and determining the pressure difference across the orifice plate. However, the flowmeter 44 is preferably made of a nonmagnetic material. Moreover, the position at which the flowmeter 44 is disposed may be anywhere between the valve 280 and mask section 210.

Next, the operation of the supplying means 5 and scan controller section 760 will be described. The supplying means 5 first measures a respiration signal by the mask section 210 attached to the subject 1, and the flow rate of xenon by the flowmeter 44. The scan controller section 760 receives these signals, and calculates the respiration cycle from the respiration signal. Furthermore, the amount of xenon gas inhaled by the subject 1 is thereafter calculated from the respiration cycle and flow rate of xenon.

Since the maximum received signal increases approximately in proportion to the amount of xenon in a hyperpolarized state inhaled by the subject 1, the coefficient of proportion is experimentally determined beforehand. From the amount of the gas inhaled by the subject 1 and the experimentally determined coefficient of proportion, an approximate magnitude of the maximum received signal is determined.

Based on the magnitude of the maximum received signal, the gain of the amplifier set at a prescan in which no xenon is inhaled can be corrected to an optimum value.

As described above, in Embodiment 3, the flowmeter 44 is attached to the tube 266 in the supplying means 5, and the accurate flow rate of xenon is measured along with a respiration signal from the detection sensor 290, and therefore, the amount of xenon gas inhaled by the subject 1 can be accurately predicted, and optimization of the gain of the amplifier, and hence, the SNR, can be achieved by the prediction.

Many widely different embodiments of the invention may be constructed without departing from the spirit and the scope of the present invention. It should be understood that the present invention is not limited to the specific embodiments described in the specification, except as defined in the appended claims.

What is claimed is:

1. A magnetic resonance imaging system comprising:
   a rare gas polarizer apparatus for supplying a rare gas in a hyperpolarized state to a subject; and
   a magnetic resonance imaging apparatus for acquiring magnetic resonance information on said subject inhaling said rare gas, said magnetic resonance imaging system characterized in that:
   said rare gas polarizer apparatus comprises a mask section;
   said rare gas polarizer apparatus has supplying section for supplying said rare gas mixed with an inspired material to said mask section closed against the outer air covering the respiratory organs of said subject;
   said supplying section has a detection sensor for detecting said respiration;
   said magnetic resonance imaging apparatus has a control processing section for conducting said acquisition or optimization of parameters for said acquisition based on respiration information from said detection sensor; and said rare gas polarizer apparatus comprises a flowmeter configured to measure a flow rate of said rare gas.

2. The magnetic resonance imaging system of claim 1, wherein said control processing section conducts said acquisition synchronously with the inspiration or expiration indicated in said respiration information.

3. The magnetic resonance imaging system of claim 2, wherein said control processing section conducts said acquisition after an additional lag time from said synchronization.

4. The magnetic resonance imaging system of claim 1, wherein said control processing section counts a number of times of respiration from said respiration information and conducts said optimization on parameters based on said number of times of respiration.

5. The magnetic resonance imaging system of claim 4, wherein said parameters include the gain of an amplifier for use in acquiring said magnetic resonance information.

6. The magnetic resonance imaging system of claim 1, wherein said control processing section conducts said optimization of parameters based on flow rate information from said flowmeter.

7. The magnetic resonance imaging system of claim 1 wherein said mask section comprises a valve configured to be closed when a space inside said mask section is at a negative pressure relative to the outer air.

* * * * *

UNITED STATES PATENT AND TRADEMARK OFFICE
CERTIFICATE OF CORRECTION

| | |
|---|---|
| PATENT NO. | : 6,963,199 B2 |
| APPLICATION NO. | : 10/881401 |
| DATED | : November 8, 2005 |
| INVENTOR(S) | : Sato |

Page 1 of 1

It is certified that error appears in the above-identified patent and that said Letters Patent is hereby corrected as shown below:

In Claim 5, column 16, line 2, delete "the gain" and insert therefor -- a gain --.

Signed and Sealed this

Sixth Day of November, 2007

JON W. DUDAS
*Director of the United States Patent and Trademark Office*